United States Patent
Larson et al.

(10) Patent No.: US 6,881,747 B2
(45) Date of Patent: Apr. 19, 2005

(54) SMALL MOLECULES FOR INHIBITION OF FUNCTION AND DRUG DELIVERY TO LEUKOCYTES

(75) Inventors: Richard S. Larson, Albuquerque, NM (US); Carston R. Wagner, St. Paul, MN (US)

(73) Assignees: Science & Technology Corporation @UNM, Albuquerque, NM (US); Regents of the University of Minnesota, Minneapolis, MN (US)

( * ) Notice: Subject to any disclaimer, the term of this patent is extended or adjusted under 35 U.S.C. 154(b) by 62 days.

(21) Appl. No.: 10/429,041

(22) Filed: May 5, 2003

(65) Prior Publication Data

US 2004/0023929 A1 Feb. 5, 2004

Related U.S. Application Data

(60) Provisional application No. 60/378,536, filed on May 6, 2002.

(51) Int. Cl.$^7$ .................. A61K 31/4166; C07D 233/02
(52) U.S. Cl. .................. 514/386; 548/317.1; 548/319.5
(58) Field of Search ........................... 548/317.1, 319.5; 514/386

(56) References Cited

U.S. PATENT DOCUMENTS 6,355,664 B1    3/2002   Kelly et al.

OTHER PUBLICATIONS

Kapadia et al., "An Improved Synthesis of Chiral α–(4–Bromobenzyl)alanine Ethyl Ester and Its Application to the Synthesis of LFA–1 Antagonist BIRT–377" *J. Org. Chem* 2001, 66: 1903–1905. .

Kelly et al., "Cutting Edge: A Small Molecule Antagonist of LFA–1–Mediated Cell Adhesion" *The Journal of Immunology* 1999, 163: 5173–5177.

Wasan et al., "Rat and Rabbit Plasma Distribution of Free and Chylomicron–Associated BIRT 377, a Novel Small Molecule Antagonist of LFA–1–Mediated Cell Adhesion" *Pharmaceutical Research* 2001, 18: 510–519.

Woska, Jr., et al., "A small–molecule antagonist of LFA–1 blocks a conformational change important for LFA–1 function" *Journal of Leukocyte Biology* 2001, 70: 329–334.

Yee, "Self–Regeneration of Stereocenters: A Practical Enantiospecific Synthesis of LFA–1 Antagonist BIRT–377" *Organic Letters* 2000, 2: 2781–2783.

*Primary Examiner*—Golam M M Shameem
(74) *Attorney, Agent, or Firm*—Henry D. Coleman; R. Neil Sudol; William J. Sapone

(57) ABSTRACT

The present invention provides a compound and a method of making a compound according to the following formula:

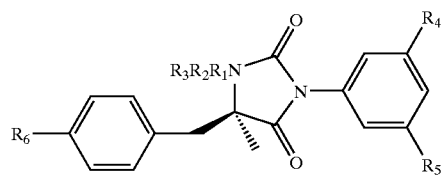

where $R_1$ is an alkyl group having 1 to 12 carbons; $R_2$ is a urea group; $R_3$ is an active group, such as fluorescein, a toxin, radiolabel or drug; and $R_4$, $R_5$ and $R_6$ are each independently a halide group.

19 Claims, No Drawings

SMALL MOLECULES FOR INHIBITION OF FUNCTION AND DRUG DELIVERY TO LEUKOCYTES

CROSS-REFERENCE TO RELATED APPLICATIONS

This application claims priority from U.S. Provisional Patent Application No. 60/378,536, entitled "Drug Discovery Systems and Methods and Compounds for Drug Delivery," filed May 6, 2002. The entire disclosure and contents of the above application is hereby incorporated by reference.

BACKGROUND OF THE INVENTION

1. Field of the Invention

The present invention relates generally to small molecules for inhibition of function of and drug delivery to leukocytes, and more particularly to small molecules that specifically recognize or have an affinity for LFA-1.

2. Description of the Prior Art

The interaction of lymphocyte function-associated antigen (LFA)-1 with its ligands, intercellular adhesion molecules ICAM-1, ICAM-2 and ICAM-3, mediates several steps leading to an inflammatory response and has an established role in leukocyte cell adhesion and further exerts its influence on cell trafficking and cell-cell contact. Woska, et al., "A small-molecule antagonist of LFA-1 blocks a conformational change important for LFA-1 function, Journal of Leukocyte Biology," 70: 329–334 (August 2001), and Kelly, et al., "Cutting Edge: A Small Molecule Antagonist of LFA-1-Mediated Cell Adhesion," Journal of Immunology, 163: 5173–5177 (1999), the entire contents and disclosures of which are hereby incorporated by reference herein. Leukocyte extravasation, antigen presentation, and T-cell effector functions are all mediated in part by LFA-1. However, most therapeutics designed to block the binding of LFA-1 to ICAM-1 have been mAb based.

Thus, there is still a need for appropriate small molecules for inhibition of function of and drug delivery to leukocytes that specifically recognize or have an affinity for LFA-1.

SUMMARY OF THE INVENTION

It is therefore an object of the present invention to provide small molecules for inhibition of function of and drug delivery to leukocytes.

It is a further object to provide small molecules that specifically recognize or have an affinity for LFA-1.

According to a first broad aspect of the present invention, there is provided a molecule comprising the following formula:

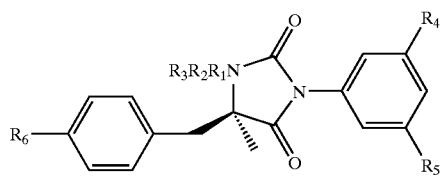

wherein $R_1$ is an alkyl group or an aryl group; $R_2$ is a urea group, phosphate group, phosphoramidate group or a sulfonate group; $R_3$ is an active group; and $R_4$, $R_5$ and $R_6$ are each independently a halide group.

According to second broad aspect of the invention, there is provided a method for forming a molecule comprising the steps of providing a compound (1) having the following formula:

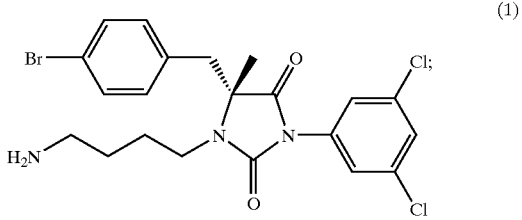

and
reacting compound (1) with fluorescein N-isothiocyanate to thereby form a compound (2) having the following formula:

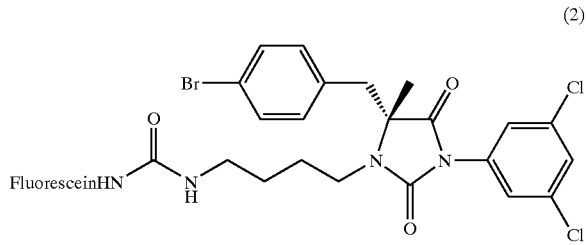

Other objects and features of the present invention will be apparent from the following detailed description of the preferred embodiment.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc ; and the like. The term "aikyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Preferably, an alkyl group comprises from 1 to 20 carbon atoms, more preferably, from 1 to 12 carbon atoms.

For the purposes of the present invention, the term "aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenialene, phenanthrene, picene, pleiadene, pyrene, pyranthrene, rubicene, triphenylene, trinaphthalene, and the like. Preferably, an aryl group comprises from 6 to 20 carbon atoms, more preferably between 6 to 12 carbon atoms.

For the purposes of the present invention, the term "active group" refers to a group that is capable of acting as a fluorophore, radiolabel, toxin or drug. A particularly useful active group is fluorescein.

For the purposes of the present invention, the term "toxin" refers to any poison or toxicant.

For the purposes of the present invention, the term "radiolabel" refers to any compound that has been joined with a radioactive substance for, e.g., certain imaging methods.

For the purposes of the present invention, the term "drug" refers to any type of substance that is commonly considered a drug. For the purposes of the present invention, a drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, for the purposes of the present invention, a drug may be a substance that affects the activity of a specific cell, bodily organ or function. A drug may be an organic or inorganic chemical, a biomaterial, etc. The term drug also refers to any molecule that is being tested as a potential precursor of a drug.

For the purposes of the present invention, the term "halide group" refers to a fluorine, chlorine, bromine or iodine group.

For the purposes of the present invention, TFAA refers to trifluoroacetic anhydride.

For the purpose of the present invention, TFA refers to trifluoroacetic acid.

For the purposes of the present invention, THF refers to tetrahydrofuran.

For the purposes of the present invention, FITC refers to fluorescein N-isothiocyanate.

For the purposes of the present invention, LiHMDS refers to lithium hexamethyldisilazide.

For the purposes of the present invention, KHMDS refers to potassium hexamethyldisilazide.

For the purposes of the present invention, LDS refers to lithium diisopropylamide.

Description

The present invention provides for small molecules and the synthesis thereof for inhibiting the function of leukocytes. In addition, these small molecules may be used for drug delivery to leukocytes.

In an embodiment of the present invention, there is provided a compound according to the following formula:

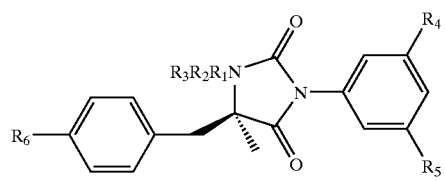

where $R_1$ is an alkyl group having 1 to 20 carbons or an aryl group having 6 to 20 carbons; $R_2$ is a urea group or other linking group such as phosphates, phosphoramidate, sulfonate, other groups including peptide bonds, carbonates, etc.; $R_3$ is an active group, such as fluorescein, a fluorophore, a toxin, a radiolabel or a drug; and $R_4$, $R_5$ and $R_6$ are each independently a halide group.

An exemplary compound of the present invention may be represented as follows:

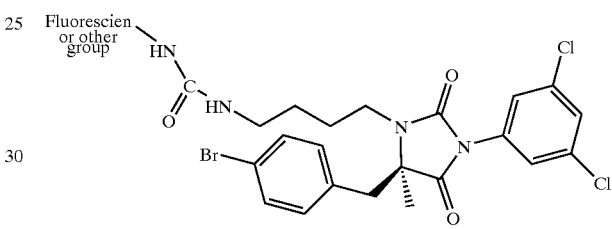

The compound shown above specifically recognizes LFA-1 and has a design suitable for use as a drug delivery vehicle or as a fluorochrome-labeled probe or imaging agent for detecting receptor activity on the surface of leukocytes. This compound has 1) an alkyl side chain that is four carbon units long, but may be of various lengths. This side chain allows attachment of additional chemical units in a manner that does not affect binding of the small molecule to LFA-1; 2) a urea group, i.e., a versatile chemical group on which a number of compounds may be attached for delivery, and 3) an active group.

Active groups of the present invention may be a fluorophore or fluorescein for real-time measurements of receptor activity, or a toxin, radiolabel or drug. This active group will deliver the biologic and physiologic effect to the target cell.

By creating this chimeric chemical structure, a compound has been created that recognizes all leukocytes and allows for efficient and specific delivery of a drug, toxin or radionucleotide to leukocytes. The molecule recognizes an antigen LFA-1. This antigen is expressed on all leukocytes in humans. It is also expressed on malignant leukemia and lymphoma cells. Therefore, this molecule will specifically bind to the LFA-1 molecule and deliver the effect of the active group to normal or malignant leukocytes. In this manner, leukocytes would be specifically destroyed with minimal affect on other tissues.

Compounds of the present invention have application to cancers of leukocytes that include acute and chronic leukemias, lymphomas, and myelodysplasias. In addition, severe immune and inflammatory responses in diseases where current therapy may not be effective may also be an application. These would include transplant rejection, among others.

The following derivatives have differing affinities for LFA-1 and may be useful for inhibition of leukocyte function in vivo or in vitro.

| | Structure | Name | $K_D$ (Affinity constant) |
|---|---|---|---|
| A | (L) | JEB I-18 | 3650 nM |
| B | (D) | JEB I-19 | 620 nM |
| C | (D) | JEB I-22 | 1230 nM |
| D | (L) | JEB I-24 | 1200 nM |
| E | 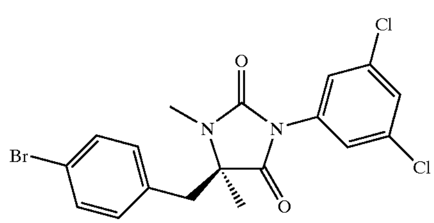 | BIRT 377 | 22 nM |
| F | 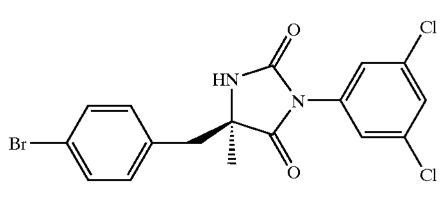 | Nor-BIRT | 30 nM |

| Structure | Name | $K_D$ (Affinity constant) |
|---|---|---|
| G | Butylamino-Nor-BIRT | 75 nM |
| H | Fluorescein-Butylamino-Nor-BIRT | 115 nM |

Molecules of the present may be used for drug delivery to leukocytes, measurement of receptor activity in a flow cytometer, measurement of inhibitory function on leukocytes, as well as other applications. When the active group is a toxin or therapeutic agent, the molecule will deliver a specific drug effect to leukocytes. When the active group is a fluorescein or other fluorophore, the molecule can be used to measure real-time receptor activity. With or without the active group, the molecule can be used to measure inhibitory function on leukocytes. When a radiolabel is attached to the leukocyte, it may be used either as an imaging or therapeutic.

EXAMPLE I

The synthesis of a preferred compound according to the present invention including a fluorescein group is shown below:

1) Preparation of boc[D]-alanine-(3,5-dichloroanilide)

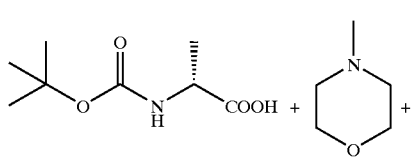

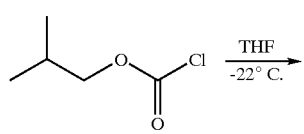

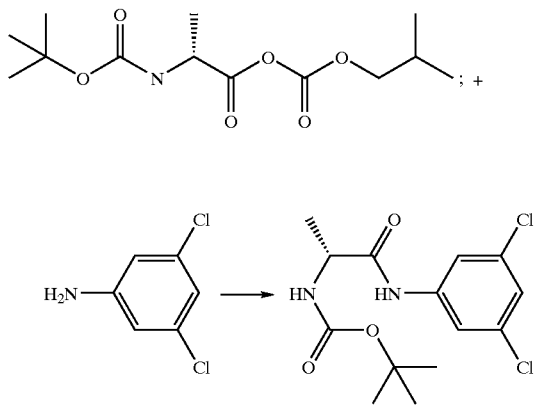

2) Hydrolysis of boc-[D]-alanine-(3,5-dichloroanilide): Preparation of [D]-alanine-(3,5-dichloroanilide)

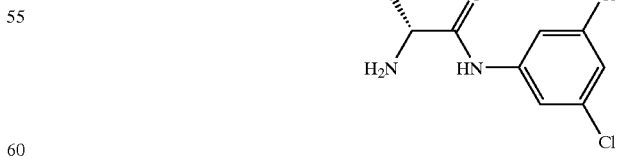

3) Condensation of pivalaldehyde with [D]-alanine-(3,5-dichloroanilide): Preparation of (trans)-(2R,5 S)-3-(3,5-dichlorophenyl)-2-t-butyl-5-methylimidazolidin-3-one

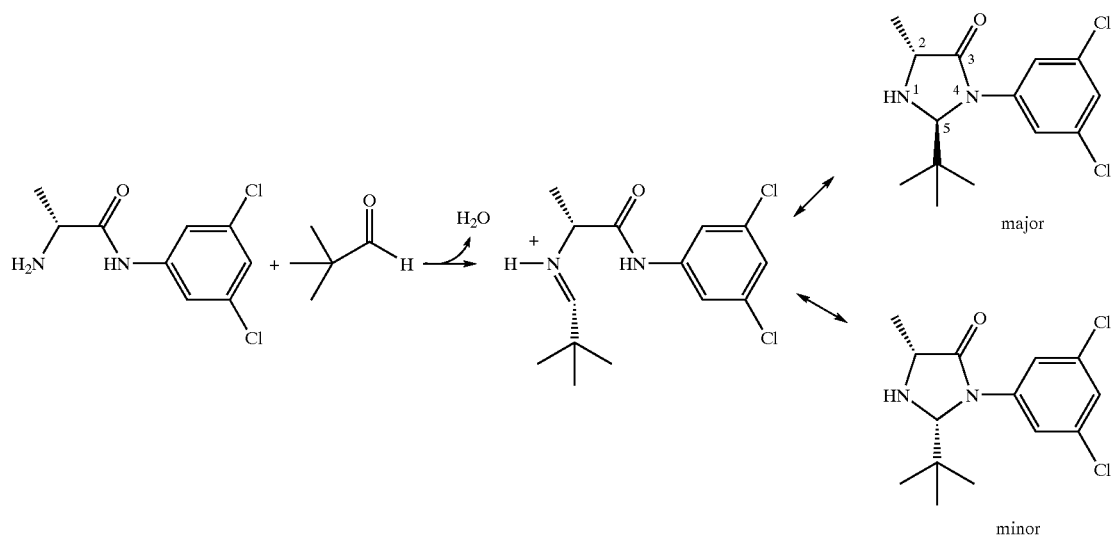

major minor

4) Trifluoroacetylation of 2-tert-butyl-3-(3,5-dichlorophenyl)-5-methyl-1-trifluoroacetyl-imidazolidin-4-one: Preparation of trans-(5R,2S)-2-tert-butyl-3-(3,5-dichlorophenyl)-5-methyl-1-trifluoroacetyl-imidazolidin-4-one

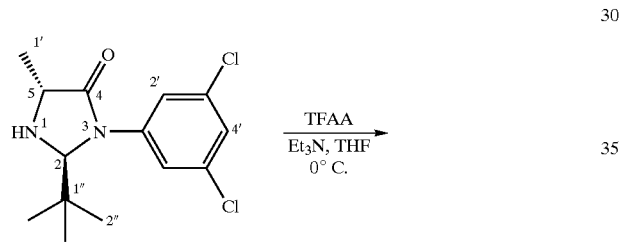

5) Bromobenzylation of trans-(5R,2R)-1-trifluoroacetyl-2-tert-butyl-3-(3,5-dichlorophenyl)-5-methyl-imidazolidin-4-one: Preparation of (5R,2R)-1-trifluoroacetyl-2-tert-butyl-3-(3,5-dichlorophenyl)-5-methyl-5-(4-bromobenzyl)-1-imidazolidin-4-one

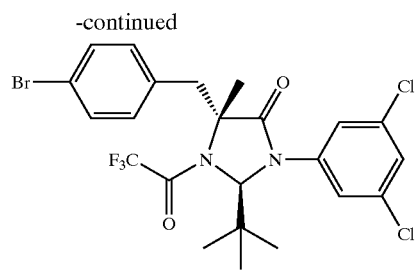

-continued

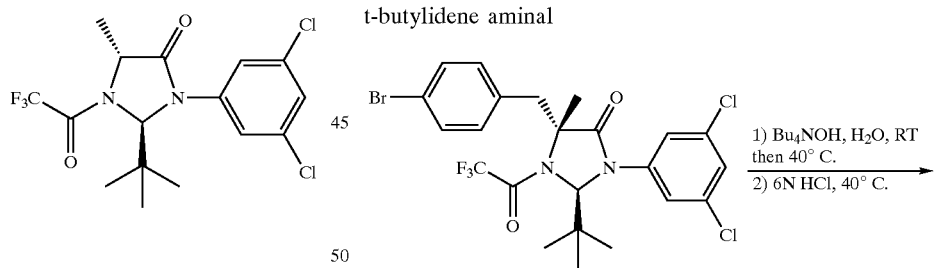

6) Hydrolytic cleavage of trifluoroacetamide and t-butylidene aminal

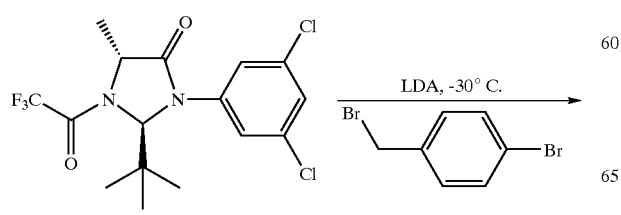

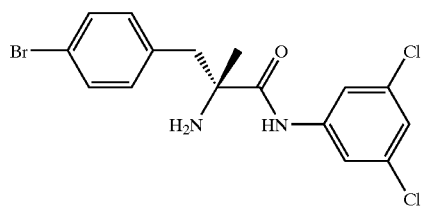

7) Ring closure of (R)-3-(4-bromobenzyl)-alanine-(3,5-dichloroanilide) to (R)-5-(4-bromobenzyl)-3-(3,5-dichlorophenyl)-5-methyl-imidazolidine-2,4-dione

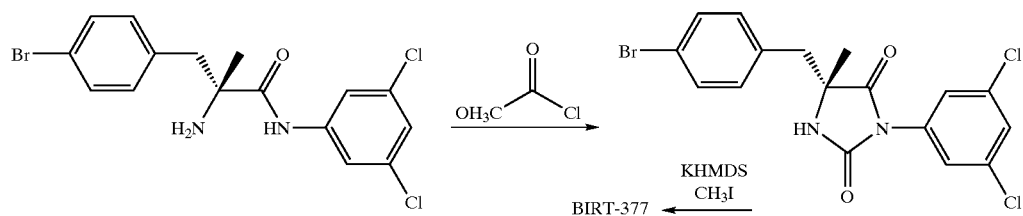

8) n-butylphthalimidation of (R)-5-(4-bromobenzyl)-3-(3,5-dichlorophenyl)-5-methyl-imidazolidine-2,4-dione

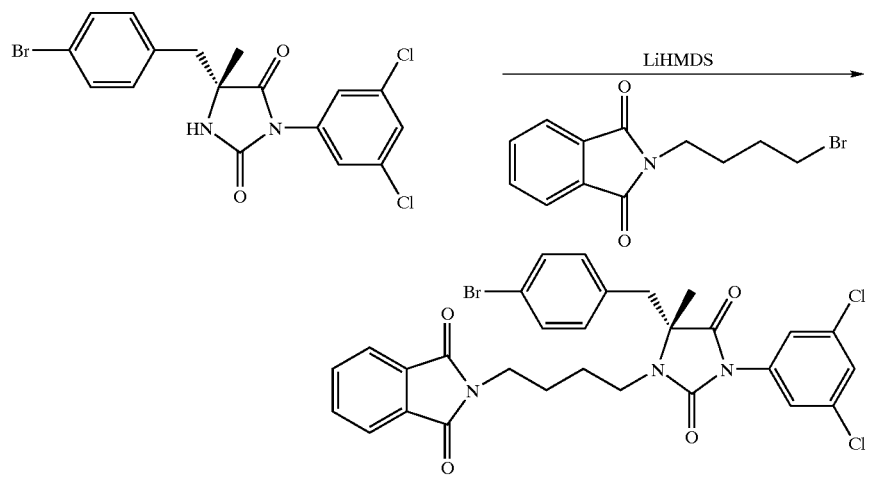

9) Cleavage of phthalimide to give 1-(4-aminobutyl)-5-(4-bromobenzyl)-3-(3,5-dichlorophenyl)-5-methyl-imidazolidine-2,4-dione

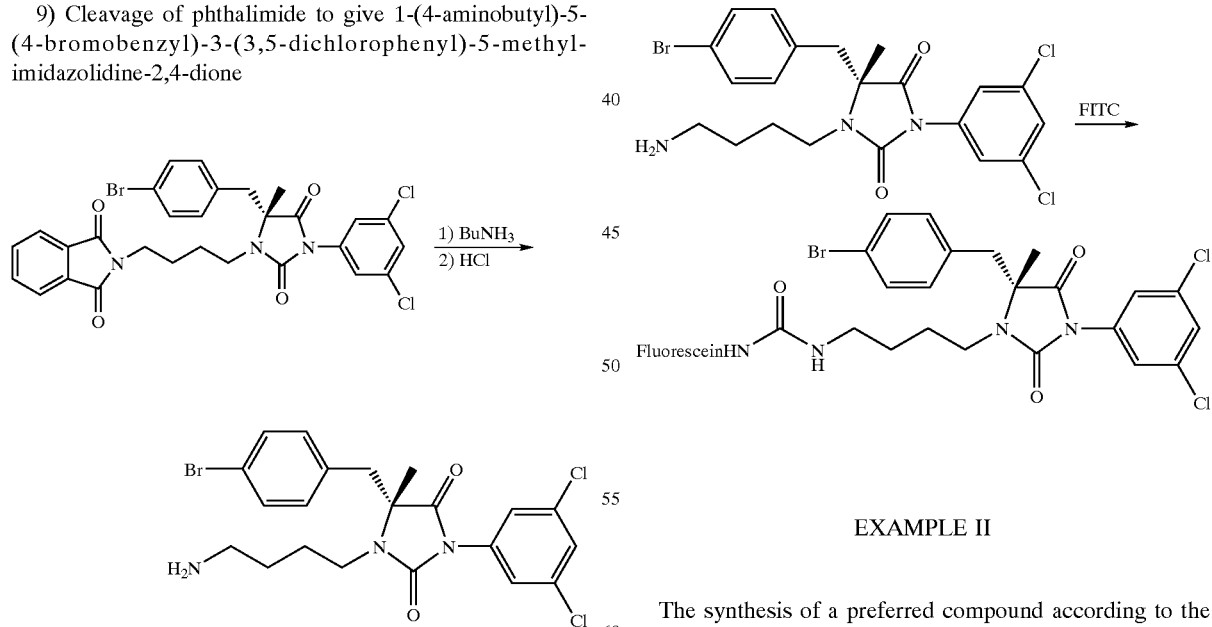

10) Coupling with FITC (fluorescein N-isothiocyanate) reagent: Preparation of 5-(4-bromobenzyl)-3-(3,5-dichlorophenyl)-5-methyl-imidazolidine-2,4-dione-1-(1-butyl-4-fluoresceincarbamide)

EXAMPLE II

The synthesis of a preferred compound according to the present invention including a radiolabel is shown below:

Steps 1–9 of Example I are performed to give 1-(4-aminobutyl)-5-(4-bromobenzyl)-3-(3,5-dichlorophenyl)-5-methyl-imidazolidine-2,4-dione. Further steps according to the above methodology may be conducted to form a compound such as:

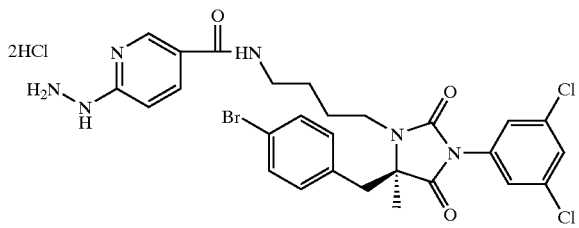

N-{4-[5-(4-Bromo-benzyl)-3-(3,5-dichloro-phenyl)-5-methyl-2,4-dioxo-imidazolidin-1-yl]-butyl}-6-hydrazino-nicotinamide Dihydrochloride This compound may further be chelated with technechium to form, for example, a radiolabel imaging compound.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A molecule according to the following formula:

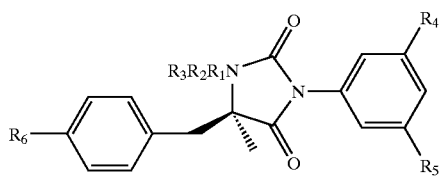

wherein $R_1$ is an alkyl group or an aryl group:

$R_2$ is a urea group, phosphate group, phosphoramidate group or a sulfonate group:

$R_3$ is an active group selected from the group consisting of fluorescein, a fluorophor, a toxin, a radiolabel and a drug; and $R_4$, $R_5$ and $R_6$ are each independently a halide group.

2. The molecule of claim 1, wherein $R_1$ is an alkyl group having 1 to 20 carbons.

3. The molecule of claim 1, wherein $R_1$ is an alkyl group having 1 to 12 carbons.

4. The molecule of claim 1, wherein $R_1$ is an aryl group having 1 to 20 carbons.

5. The molecule of claim 1, wherein $R_1$ is an aryl group having 1 to 12 carbons.

6. The molecule of claim 1, wherein $R_2$ is a urea group.

7. The molecule of claim 1, wherein $R_2$ is a phosphate group.

8. The molecule of claim 1, wherein $R_2$ is a phosphoramidate group.

9. The molecule of claim 1, wherein $R_2$ is a sulfonate group.

10. The molecule of claim 1, wherein $R_3$ is a fluorophore.

11. The molecule of claim 1, wherein $R_3$ is fluorescein.

12. The molecule of claim 1, wherein $R_3$ is a toxin.

13. The molecule of claim 1, wherein $R_3$ is a radiolabel.

14. The molecule of claim 1, wherein $R_3$ is a drug.

15. The molecule of claim 1, wherein at least one of $R_4$, $R_5$ and $R_6$ is bromine.

16. The molecule of claim 1, wherein at least one of $R_4$, $R_5$ and $R_6$ is chlorine.

17. The molecule of claim 1, wherein $R_6$ is bromine.

18. The molecule of claim 1, wherein $R_4$ and $R_5$ are chlorine.

19. A molecule according to the following formula:

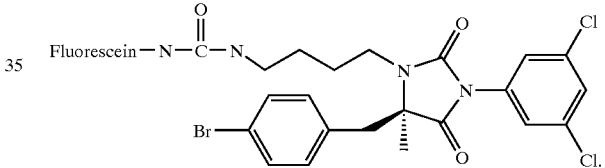

* * * * *